United States Patent
Yamamoto

(10) Patent No.: US 9,296,675 B2
(45) Date of Patent: Mar. 29, 2016

(54) COMPOUND HAVING CYCLOPROPANE RING, AND FLAVOR AND/OR FRAGRANCE COMPOSITION CONTAINING SAME

(71) Applicant: TAKASAGO INTERNATIONAL CORPORATION, Tokyo (JP)

(72) Inventor: Kenichi Yamamoto, Hiratsuka (JP)

(73) Assignee: TAKASAGO INTERNATIONAL CORPORATION, Tokyo (JP)

(*) Notice: Subject to any disclaimer, the term of this patent is extended or adjusted under 35 U.S.C. 154(b) by 0 days.

(21) Appl. No.: 14/760,744

(22) PCT Filed: Mar. 7, 2014

(86) PCT No.: PCT/JP2014/055956
§ 371 (c)(1),
(2) Date: Jul. 14, 2015

(87) PCT Pub. No.: WO2014/142025
PCT Pub. Date: Sep. 18, 2014

(65) Prior Publication Data
US 2015/0353461 A1  Dec. 10, 2015

(30) Foreign Application Priority Data
Mar. 12, 2013 (JP) .................. 2013-048678

(51) Int. Cl.
| | | |
|---|---|---|
| C07C 47/293 | (2006.01) | |
| C07C 31/13 | (2006.01) | |
| C11B 9/00 | (2006.01) | |
| C07C 47/105 | (2006.01) | |
| A23L 1/226 | (2006.01) | |
| C07C 33/34 | (2006.01) | |
| D06M 13/127 | (2006.01) | |
| D06M 13/144 | (2006.01) | |
| A23L 2/56 | (2006.01) | |
| D06M 13/00 | (2006.01) | |

(52) U.S. Cl.
CPC ............ *C07C 47/293* (2013.01); *A23L 1/2265* (2013.01); *A23L 1/22657* (2013.01); *A23L 2/56* (2013.01); *C07C 31/13* (2013.01); *C07C 33/34* (2013.01); *C07C 47/105* (2013.01); *C11B 9/003* (2013.01); *C11B 9/0061* (2013.01); *D06M 13/005* (2013.01); *D06M 13/127* (2013.01); *D06M 13/144* (2013.01); *A23V 2002/00* (2013.01); *C07C 2101/02* (2013.01); *C07C 2101/16* (2013.01)

(58) Field of Classification Search
CPC ...... C07C 33/74; C07C 47/395; C07C 31/13; C07C 2101/02; C07C 2101/16; A23L 1/2205
USPC .................................................. 568/425, 807
See application file for complete search history.

(56) References Cited

U.S. PATENT DOCUMENTS

| | | |
|---|---|---|
| 3,862,340 A | 1/1975 | Schreiber et al. |
| 2005/0119156 A1 | 6/2005 | Turin |
| 2010/0069508 A1 | 3/2010 | Bajgrowicz |
| 2012/0208741 A1 | 8/2012 | Moretti |
| 2015/0038386 A1 | 2/2015 | Dang et al. |

FOREIGN PATENT DOCUMENTS

| | | |
|---|---|---|
| JP | 63-183522 A | 7/1988 |
| JP | 63-227546 A | 9/1988 |
| JP | 2006-506316 A | 2/2006 |
| WO | 2011/051834 A1 | 5/2011 |
| WO | 2012/160189 A1 | 11/2012 |

OTHER PUBLICATIONS

Liao et al. A Copper-Catalyzed Method for the Facially Selective Addition of Grignard Reagents to Cyclopropanes. Journal of the American Chemical Society, 2002, vol. 124, 14322-14323.*
Janine Cossy et al., "Stereoselective Synthesis of Cyclopropanes Bearing Adjacent Stereocenters", Synthesis 1999, pp. 1063-1075, No. 6.
International Searching Authority, International Search Report of PCT/JP2014/055956 dated Jun. 3, 2014 [PCT/ISA/210].

* cited by examiner

*Primary Examiner* — Sikarl Witherspoon
(74) *Attorney, Agent, or Firm* — Sughrue Mion, PLLC

(57) ABSTRACT

Provided are a compound of formula (1), having a cyclopropane ring, which can impart a floral or citrus-like aroma and a flavor composition containing at least one compound of formula (1):

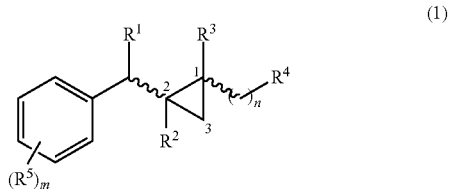

(1)

wherein, $R^1$, $R^2$, $R^3$ and $R^5$ independently represent a hydrogen atom or an alkyl group having 1 to 3 carbon atoms, wherein at least two groups among $R^1$, $R^2$, $R^3$ and $R^5$ independently represent an alkyl group; $R^4$ represents a group selected from a formyl group, a hydroxymethyl group, a 1-hydroxy-1-ethyl group, a 1-hydroxy-1-propyl group, a 1-hydroxy-1-butyl group and a 2-hydroxy-1-propyl group; m represents 0 to 2; n represents 0 or 1; and a wavy line stands for a cis-configuration, a trans-configuration or a mixture of a cis-configuration and a trans-configuration with respect to position-2 on a cyclopropane ring.

7 Claims, No Drawings

COMPOUND HAVING CYCLOPROPANE RING, AND FLAVOR AND/OR FRAGRANCE COMPOSITION CONTAINING SAME

CROSS REFERENCE TO RELATED APPLICATIONS

This application is a National Stage of International Application No. PCT/JP2014/055956, filed Mar. 7, 2014, claiming priority based on Japanese Patent Application No. 2013-048678, filed Mar. 12, 2013, the contents of all of which are incorporated herein by reference in their entirety.

TECHNICAL FIELD

The present invention relates to a flavor and/or fragrance composition containing a compound having a cyclopropane ring.

BACKGROUND ART

Some compounds having a cyclopropane ring are known to be useful as raw materials for flavor compositions and/or fragrance compositions. For example, [1-methyl-2-(5-methyl-4-hexen-2-yl)cyclopropyl]methanol has an odor similar to those of citrus and 3-methyl-5-phenyl-1-pentanol, with rosy floral note (WO 2012/160189 A1). Meanwhile, 1-methyl-2-[(2,2,3-trimethylcyclopentyl)methyl]cyclopropyl]methanol has a natural sandalwood-like odor (US 2010/0069508 A1). In addition, 2-(1-phenylethyl)cyclopropylmethanol and the like are known as compounds having a cyclopropane ring and a benzene ring, but their odors are not mentioned (Synthesis (1999), No. 6, 1063-1075).

SUMMARY OF INVENTION

With the recent diversification of products such as various cosmetics, health and sanitary articles, and pharmaceuticals, development of a flavor and/or fragrance substance having high diffusibility, unique odor quality, highly preferred characteristics, long lasting, good stability, and high safety as a flavor and/or fragrance for them has been demanded more eagerly than before. Especially, regarding flavor and/or fragrance materials having a floral or citrus-like odor, only an insufficient number of compounds satisfy such requirements, and besides the conventionally known substances, development of a novel material satisfying the above-described characteristics has been awaited.

Accordingly, an object of the present invention is to provide a compound capable of imparting a floral or citrus-like odor satisfying the above-described requirements.

Under such circumstances, the present inventors have conducted intensive study, and consequently have found that a compound obtained by subjecting an allyl alcohol derivative to cyclopropane formation has a strong floral or citrus-like odor, and can serve as a useful odor-imparting agent. This finding has led to the completion of the present invention.

Specifically, the present invention includes the following contents [1] to [7].

[1] A compound represented by Formula (1):

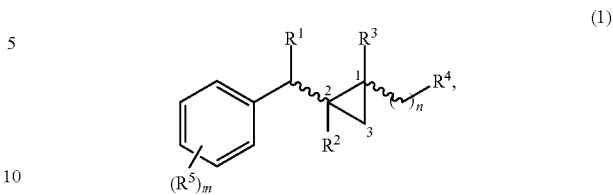

wherein $R^1$, $R^2$, $R^3$, and $R^5$ each represent a hydrogen atom or an alkyl group having 1 to 3 carbon atoms, provided that two or more groups of $R^1$, $R^2$, $R^3$, and $R^5$ are alkyl groups;

$R^4$ represents a group selected from a formyl group, a hydroxymethyl group, a 1-hydroxy-1-ethyl group, a 1-hydroxy-1-propyl group, a 1-hydroxy-1-butyl group, and a 2-hydroxy-1-propyl group;

m is 0 to 2;

n is 0 or 1; and the wavy lines indicate a cis-configuration, a trans-configuration, or a mixture of a cis-configuration and a trans-configuration with respect to position-2 on the cyclopropane ring.

[2] The compound according to the above-described [1], wherein $R^4$ is a group selected from a hydroxymethyl group, a 1-hydroxy-1-ethyl group, a 1-hydroxy-1-propyl group, a 1-hydroxy-1-butyl group, and a 2-hydroxy-1-propyl group.

[3] The compound according to the above-described [2], wherein $R^1$ and $R^3$ are both methyl groups.

[4] The compound according to the above-described [2], wherein $R^1$, $R^2$, and $R^3$ are all methyl groups.

[5] The compound according to the above-described [2] to [4], wherein $R^5$ is a methyl group.

[6] A flavor and/or fragrance composition, comprising:

at least one of the compounds according to the above-described [1] to [5].

[7] A food or beverage, a cosmetic, an air-freshener, a daily necessity or grocery, an oral cavity composition, a hair-care product, a skin-care product, a body-cleaning agent, a laundry detergent, a laundry softener, a toiletry product, a fiber or fiber product, a garment, or a pharmaceutical, comprising the flavor and/or fragrance composition according to the above-described [6].

The compound of the present invention is a very useful flavor and/or fragrance material which is highly preferred, is also excellent in odor-imparting characteristics, and is excellent in diffusibility and long lasting. By blending such a compound of the present invention, an agent for imparting a highly preferred odor can be provided.

DESCRIPTION OF EMBODIMENTS

A compound of the present invention is represented by Formula (1):

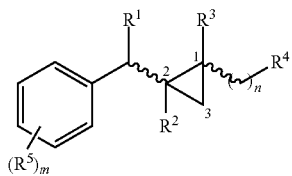

(1)

In Formula (1), $R^1$, $R^2$, $R^3$, and $R^5$ each represent a hydrogen atom or an alkyl group having 1 to 3 carbon atoms, provided that two or more groups of $R^1$, $R^2$, $R^3$, and $R^5$ are alkyl groups. The alkyl group having 1 to 3 carbon atoms is, for example, a methyl group. $R^4$ represents a group selected from a formyl group, a hydroxymethyl group, a 1-hydroxy-1-ethyl group, a 1-hydroxy-1-propyl group, a 1-hydroxy-1-butyl group, and a 2-hydroxy-1-propyl group. $R^4$ is, for example, selected from a formyl group, a hydroxymethyl group, and a 1-hydroxy-1-ethyl group. m is 0 to 2, and, for example, 0 or 1. n is 0 or 1. The wavy lines indicate a cis-configuration, a trans-configuration, or a mixture of a cis-configuration and a trans-configuration with respect to position-2 on the cyclopropane ring.

A compound of Formula (1), where n is 0, and $R^4$ is a hydroxymethyl group, is synthesized, for example, by a method shown below.

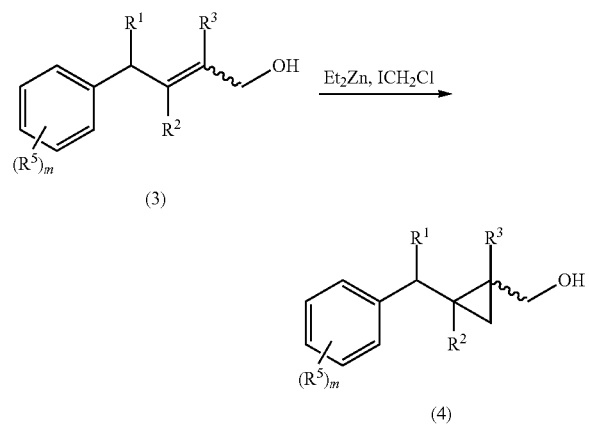

(3)

(4)

First, an allyl alcohol derivative (3) is reacted with a carbenoid prepared from diethylzinc and chloroiodomethane to synthesize a compound (4) having a cyclopropane ring. The compound (4) having a cyclopropane ring is obtained as a mixture of diastereomers having the relative configurations shown below, and the odor threshold of (4b) is lower than that of (4a).

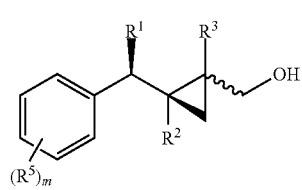

(4a)

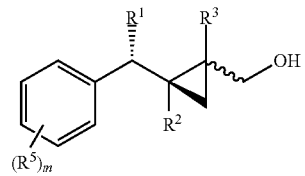

(4b)

A compound of Formula (1), where n is 0, m is 0, $R^1$ and $R^3$ are methyl groups, and $R^4$ is a 1-hydroxy-1-ethyl group, is synthesized, for example, by a method shown below.

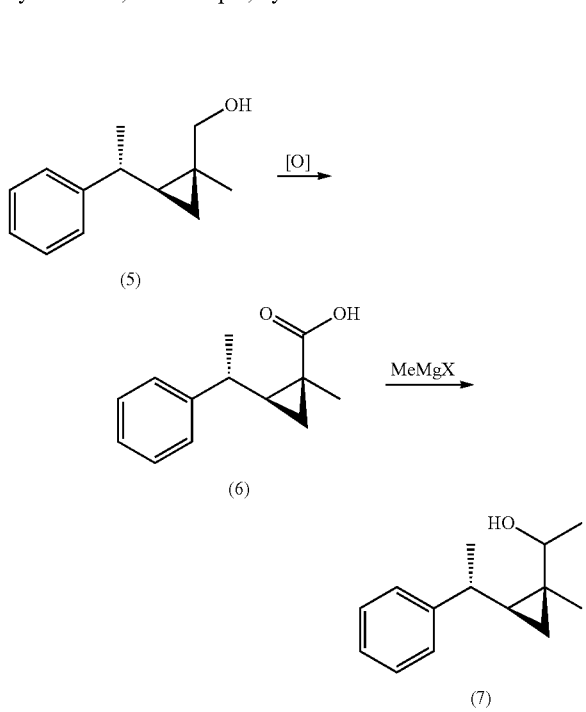

(5)

(6)

(7)

First, a compound (5) having a cyclopropane ring is oxidized to obtain an aldehyde compound (6), which is then subjected to a Grignard reaction. Thus, a compound (7) can be synthesized. Reactions usable as a method for the oxidation include the TEMPO oxidation, the Uemura Oxidation, the Albright-Goldman oxidation, the Mukaiyama oxidation, the Ley-Griffith oxidation, the Swern oxidation, and the like. The compound (7) having a cyclopropane ring is obtained as a mixture of isomers having relative configurations shown below. The odor threshold of (R*)-1-[(1S*,2S*)-1-methyl-2-((R*)-1-phenylethyl)cyclopropyl]ethanol (7a) is 100 times or more lower than that of (S*)-1-[(1S*,2S*)-1-methyl-2-((R*)-1-phenylethyl)cyclopropyl]ethanol (7b).

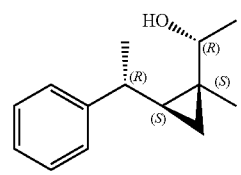

(7a)

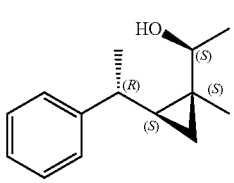

A compound having a cyclopropane ring of Formula (1), where n is 1, m is 0, R¹ and R³ are methyl groups, and R⁴ is a formyl group, is synthesized, for example, by a method shown below.

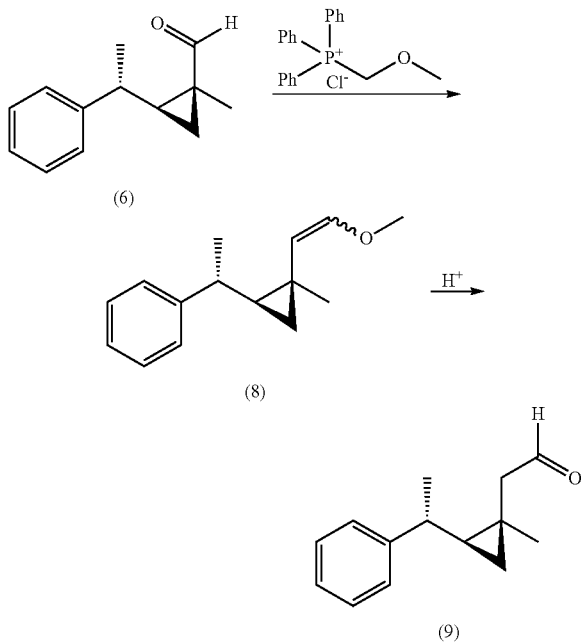

First, a compound (6) is subjected to the Wittig reaction to synthesize an enol ether (8). The obtained enol ether is hydrolyzed in the presence of an acid catalyst. Thus, a compound (9) having a cyclopropane ring can be easily synthesized. Acids used here include acetic acid, citric acid, hydrochloric acid, sulfuric acid, and the like.

If necessary, the thus obtained compound of the present invention can be isolated and purified. Examples of methods for the isolation and purification include column chromatography, vacuum distillation, crystallization, and the like. These methods can be carried out alone or in combination.

The amount of the compound represented by Formula (1) blended in a flavor and/or fragrance composition is not particularly limited, and is preferably 0.01 to 60% by weight, and particularly preferably 0.1 to 40% by weight, relative to the flavor and/or fragrance composition.

In addition, any commonly used blended flavor and/or fragrance can be blended in the flavor and/or fragrance composition of the present invention. The thus obtained flavor and/or fragrance composition can impart a fresh and highly preferred odor. Moreover, the flavor and/or fragrance composition of the present invention can be blended, as an odor component, in foods and beverages, cosmetics, air-fresheners, daily necessities and groceries, oral cavity compositions, hair-care products, skin-care products, body-cleaning agents, laundry detergents, laundry softeners, toiletry products, fibers and fiber products, garments, pharmaceuticals, and the like. Specifically, the flavor and/or fragrance composition of the present invention can be blended in shampoos, rinses, perfumes, colognes, hair tonics, hair creams, pomades, base materials for other hair cosmetics, soaps, dish washing detergents, laundry detergents, softeners, sterilizing detergents, deodorant detergents, room air-fresheners, disinfectants, pesticides, bleaching agents, other various health and sanitary detergents, dentifrices, mouthwashes, toilet papers, odor-imparting agents for facilitating ingestion of pharmaceuticals, and the like in amounts generally employed in these industrial fields. In this manner, its unique odor can be imparted to these products, and the values of the products can be enhanced.

EXAMPLES

Hereinafter, the present invention will be described in detail by way of Examples. However, the present invention is not limited to these examples at all. Note that, in Examples, the values of physical properties were measured by using the following instruments and devices.

NMR was measured by using DRX500 manufactured by Bruker. CDCl₃ was used as the solvent, and the chemical shifts were referenced to TMS and expressed in ppm. The coupling constants J were expressed in Hz.

GC/MS was measured by using an HP 6890 GC system and an HP5973MS detector of Agirent Technologies. The column used was InertCap 1 (manufactured by GL Sciences Inc., 30 m in length×0.25 mm in inner diameter, liquid-phase film thickness: 0.25 μm). The injection port temperature was 250° C., and the detector temperature was 250° C. The conditions of the temperature rise were as follows: 100° C. (15° C./minute) 300° C.

The GC purity was measured by using a 7890A GC system of Agirent Technologies. The column used was InertCap 1 (manufactured by GL Sciences Inc., 20 m in length×0.18 in mm inner diameter, liquid-phase film thickness: 0.18 μm). The injection port temperature was 250° C., and the detector temperature was 250° C. The conditions of the temperature rise were as follows: 100° C. (15° C./minute) 230° C.

Example 1

Synthesis of
1-Methyl-2-(1-phenylethyl)cyclopropylmethanol

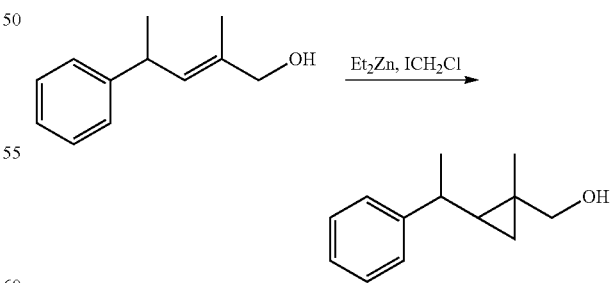

Under a nitrogen atmosphere, a diethylzinc solution in toluene (concentration: 15% by weight, 37.9 g, 46.0 mmol) was placed into a 200-ml flask equipped with a stirring apparatus, a dropping funnel, and a thermometer, and cooled to −20° C. Chloroiodomethane (16.22 g, 92.0 mmol) was placed into the dropping funnel, and added dropwise with the temperature kept between −15 to −20° C. After completion of the dropwise addition, the mixture was stirred at −10 to −15° C. for 30 minutes, and then cooled to −25° C. (E)-2-Methyl-4-phenylpent-2-ene-1-ol (4.11 g, 23.3 mmol) was added dropwise over a period of 60 minutes in the range from −20 to −25° C. After completion of the dropwise addition, the stirring was continued at −15 to −25° C. for 60 minutes. Next, a 20% aqueous sulfuric acid solution (17.0 ml) was added. After stirring for 10 minutes, the aqueous layer was separated. The organic layer was washed twice with water (20 ml), and the solvent was recovered under reduced pressure to obtain a condensed residue. This residue was purified by silica gel column chromatography (hexane:ethyl acetate=8:2). [(1R*, 2S*)-1-Methyl-2-((R*)-1-phenylethyl)cyclopropyl]methanol (1.85 g, 9.74 mmol, 42% yield) was obtained as the main isomer, and [(1R*,2S*)-1-methyl-2-((S*)-1-phenylethyl)cyclopropyl]methanol (0.55 g, 2.9 mmol, 12% yield) was obtained as a minor isomer. The relative configurations of the main isomer and the minor isomer were determined by NOESY measurement.

Main Isomer

GC/MS (m/e):

190 (M+, <1), 172 (1), 159 (7), 146 (9), 131 (17), 118 (80), 117 (100), 106 (60), 105 (80), 91 (45), 77 (20)

$^1$H (500 MHz, CDCl$_3$):

7.31 (ddm, J=8.3, 7.1, 2H), 7.27 (dm, J=8.3, 2H), 7.20 (tm, J=7.1, 1H), 3.41 (d, J=11.0, 1H), 3.35 (d, J=11.0, 1H), 2.31 (dq, J=10.6, 7.0, 1H), 1.34 (d, J=7.0, 3H), 1.28 (s, 3H), 0.87 (ddd, J=10.6, 8.8, 5.7, 1H), 0.52 (dd, J=8.8, 4.9, 1H), 0.12 (dd, J=5.7, 4.9, 1H)

$^{13}$C (125 MHz, CDCl$_3$)

147.2(s), 128.3(d), 126.0(d), 126.0(d), 72.4(t), 39.8(d), 29.7(d), 23.6(s), 22.6(q), 16.6(t), 15.3(q)

Minor Isomer

GC/MS (m/e):

190 (M+, <1), 172 (1), 159 (7), 146 (5), 131 (17), 118 (80), 117 (100), 106 (60), 105 (80), 91 (45), 77 (20)

$^1$H (500 MHz, CDCl$_3$):

7.29 (ddm, J=8.3, 7.1, 2H), 7.26 (dm, J=8.3, 2H), 7.18 (tm, J=7.1, 1H), 3.33 (d, J=10.4, 1H), 3.27 (d, J=10.4, 1H), 2.34 (dq, J=10.5, 7.0, 1H), 1.35 (d, J=7.0, 3H), 1.06 (s, 3H), 0.97 (ddd, J=10.5, 8.9, 5.5, 1H), 0.70 (dd, J=8.9, 4.7, 1H), 0.18 (dd, J=5.5, 4.7, 1H)

$^{13}$C (125 MHz, CDCl$_3$)

147.7(s), 128.4(d), 126.6(d), 125.9(d), 72.2(t), 40.0(d), 29.2(d), 23.4(s), 23.3(q), 16.5(t), 15.7(q)

Example 2

Synthesis of 1-Methyl-2-(1-phenylethyl)cyclopropylmethanol

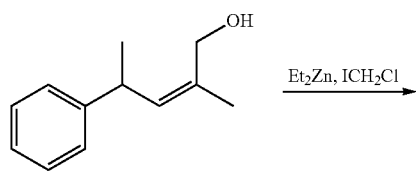

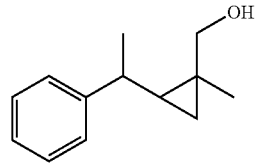

Under a nitrogen atmosphere, a diethylzinc solution in toluene (concentration: 15% by weight, 69.8 g, 84.8 mmol) was placed into a 100-ml flask equipped with a stirring apparatus, a dropping funnel, and a thermometer, and cooled to −20° C. Chloroiodomethane (29.9 g, 169.6 mmol) was placed into the dropping funnel, and added dropwise with the temperature kept between −15 and −20° C. After completion of the dropwise addition, the mixture was stirred at −10 to −15° C. for 30 minutes, and then cooled to −25° C. (Z)-2-Methyl-4-phenylpent-2-ene-1-ol (7.59 g, 42.4 mmol) was added dropwise over a period of 60 minutes in the range from −20 to −25° C. After completion of the dropwise addition, the stirring was continued at −15 to −25° C. for 60 minutes. Next, a 20% aqueous sulfuric acid solution (31.3 ml) was added. After stirring for 10 minutes, the aqueous layer was separated. The organic layer was washed twice with water (30 ml), and the solvent was recovered under reduced pressure to obtain a condensed residue. This residue was purified by silica gel column chromatography (hexane:ethyl acetate=8:2). [(1S*, 2S*)-1-Methyl-2-((R*)-1-phenylethyl)cyclopropyl]methanol (4.93 g, 25.9 mmol, 61% yield) was obtained as the main isomer, and [(1S*,2S*)-1-methyl-2-((S*)-1-phenylethyl)cyclopropyl]methanol (0.61 g, 3.2 mmol, yield 7.5%) was obtained as a minor isomer. The relative configurations of the main isomer and the minor isomer were determined by NOESY measurement.

Main Isomer

GC/MS (m/e):

172 (M+−H$_2$O, 1), 157 (5), 146 (20), 131 (27), 118 (72), 117 (100), 106 (65), 105 (75), 91 (53), 77 (25)

$^1$H (500 MHz, CDCl$_3$):

7.30 (ddm, J=7.9, 7.2, 2H), 7.25 (dm, J=7.9, 2H), 7.19 (tm, J=7.2, 1H), 3.70 (m, 2H), 2.35 (dq, J=10.6, 7.0, 1H), 1.38 (d, J=7.0, 3H), 1.30 (m, OH), 1.21 (s, 3H), 0.94 (ddd, J=10.6, 8.4, 5.9, 1H), 0.45 (dd, J=8.4, 4.8, 1H), 0.21 (dd, J=5.9, 4.8, 1H)

$^{13}$C (125 MHz, CDCl$_3$) 147.3(s), 128.3(d), 126.9(d), 125.9 (d), 67.1(t), 40.0(d), 33.3(d), 23.5(s), 23.0(q), 22.9(q), 17.3(t)

Minor Isomer

GC/MS (m/e):

190 (M+, <1), 172 (4), 157 (10), 143 (7), 131 (17), 118 (72), 117 (100), 106 (65), 105 (67), 91 (44), 77 (20) $^1$H (500 MHz, CDCl$_3$):

7.32 (ddm, J=8.3, 7.1, 2H), 7.28 (dm, J=8.3, 2H), 7.21 (tm, J=7.1, 1H), 3.52 (dd, J=11.6, 9.1, 1H), 3.33 (d, J=11.6, 1H), 2.34 (dq, J=10.6, 6.9, 1H), 1.34 (d, J=6.9, 3H), 1.13 (s, 3H), 1.06 (ddd, J=10.6, 8.3, 5.5, 1H), 0.66 (dd, J=8.3, 4.6, 1H), 0.40 (m, OH), 0.27 (dd, J=5.5, 4.6, 1H)

$^{13}$C (125 MHz, CDCl$_3$)

147.7(s), 128.8(d), 126.4(d), 126.4(d), 67.3(t), 40.9(d), 31.9(d), 24.1(q), 23.1(s), 22.6(q), 17.8(t)

Example 3

Synthesis of (1S*,2S*)-1-Methyl-2-[(R*)-1-phenylethyl]cyclopropane carbaldehyde

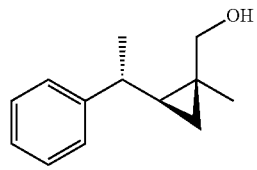

Under a nitrogen atmosphere, [(1S*,2S*)-1-methyl-2-((R*)-1-phenylethyl)cyclopropyl]methan of (1.02 g, 5.37 mmol), potassium bromide (0.36 g), 2,2,6,6-tetramethylpiperidine 1-oxyl free radical (0.085 g), and toluene (10 ml) were placed into a 100-ml flask equipped with a stirring apparatus, a dropping funnel, and a thermometer, and cooled to 0° C. An aqueous sodium hypochlorite solution (concentration: approximately 13.5%, 5.0 g, 9.1 mmol) was placed into the dropping funnel, and added dropwise with the temperature kept at 0° C. After completion of the dropwise addition, the temperature was raised to 18° C. over a period of 60 minutes. After that, the aqueous layer was separated, and the organic layer was washed with a 10% aqueous sodium thiosulfate solution and with water. The solvent was recovered under reduced pressure to obtain a condensed residue, (1S*,2S*)-1-methyl-2-[(R*)-1-phenylethyl]cyclopropane carbaldehyde (0.91 g, 4.8 mmol, 89% yield).

GC/MS (m/e):

188 (M$^+$, 5), 159 (7), 141 (5), 128 (20), 118 (82), 117 (100), 115 (45), 105 (43), 91 (60), 83 (60), 77 (44)

$^1$H (500 MHz, CDCl$_3$):

9.37 (s, 1H), 7.34 (ddm, J=8.3, 7.2, 2H), 7.28 (dm, J=8.3, 2H), 7.24 (tm, J=7.2, 1H), 2.71 (dq, J=10.4, 7.0, 1H), 1.51-1.42 (m, 2H), 1.32 (s, 3H), 1.30 (d, J=7.0, 3H), 1.09 (dd, J=7.5, 4.6, 1H)

$^{13}$C (125 MHz, CDCl$_3$)

202.7(d), 145.6(s), 128.5(d), 126.7(d), 126.5(d), 40.1(d), 38.8(d), 32.9(s), 22.5(t), 21.9(q), 18.4(q)

Example 4

Synthesis of 1-[(1S*,2S*)-1-Methyl-2-((R*)-1-phenylethyl)cyclopropyl]ethanol

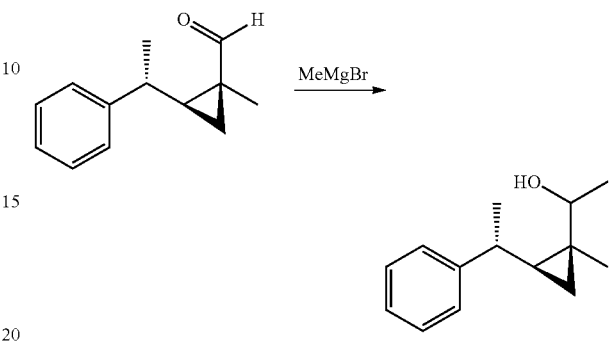

Under a nitrogen atmosphere, methyl magnesium bromide (0.97 mol/L, tetrahydrofuran solution, 8.5 ml, 8.25 mmol) was placed into a 100-ml flask equipped with a stirring apparatus, a dropping funnel, and a thermometer, and cooled to −10° C. (1S*,2S*)-1-Methyl-2-[(R*)-1-phenylethyl]cyclopropane carbaldehyde (1.03 g, 5.5 mmol) was placed into the dropping funnel, and added dropwise in 5 minutes with the temperature kept at −10° C. After stirring for 60 minutes, a 20% aqueous sulfuric acid solution (4.5 g) was added. After stirring for 10 minutes, the aqueous layer was separated, and the organic layer was washed twice with water (10 ml). The solvent was recovered under reduced pressure to obtain a condensed residue. This residue was purified by silica gel column chromatography (hexane:ethyl acetate=10:1). (R*)-1-[(1S*,2S*)-1-Methyl-2-((R*)-1-phenylethyl)cyclopropyl]ethanol (0.75 g, 3.68 mmol, 67% yield) was obtained as the main isomer, and (S*)-1-[(1S*,2S*)-1-methyl-2-((R*)-1-phenylethyl)cyclopropyl]ethanol (0.205 g, 1.0 mmol, 18% yield) was obtained as a minor isomer. The relative configurations of the main isomer and the minor isomer were determined by NOESY measurement.

Main Isomer

GC/MS (m/e):

186 (M$^+$−H$_2$O, 1), 171 (6), 160 (15), 145 (7), 131 (29), 118 (87), 117 (100), 106 (68), 105 (86), 91 (53), 77 (26), 72 (30), 70 (30)

$^1$H (500 MHz, CDCl$_3$):

7.29 (ddm, J=8.3, 7.2, 2H), 7.24 (dm, J=8.3, 2H), 7.19 (tm, J=7.2, 1H), 3.60 (q, J=6.4, 1H), 2.46 (dq, J=10.4, 6.9, 1H), 1.46 (d, J=6.9, 3H), 1.31 (d, 6.4, 3H), 1.09 (s, 3H), 0.92 (ddd, J=10.4, 8.5, 5.9, 1H), 0.41 (dd, J=8.5, 4.9, 1H), 0.01 (dd, J=5.9, 4.9, 1H)

$^{13}$C (125 MHz, CDCl$_3$)

147.7(s), 128.3(d), 127.0(d), 125.9(d), 70.5(d), 39.0(d), 34.5(d), 26.5(s), 23.6(q), 20.5(q), 18.4(q), 17.5(t)

Minor Isomer

GC/MS (m/e):

186 (M$^+$−H$_2$O, 1), 171 (7), 160 (13), 145 (7), 131 (32), 118 (85), 117 (100), 106 (65), 105 (84), 91 (55), 77 (27), 72 (21), 70 (29)

$^1$H (500 MHz, CDCl$_3$):

7.30 (ddm, J=8.3, 7.2, 2H), 7.21 (dm, J=8.3, 2H), 7.19 (tm, J=7.2, 1H), 3.58 (q, J=6.4, 1H), 2.39 (dq, J=10.5, 6.9, 1H), 1.37 (d, J=6.4, 3H), 1.36 (d, 6.9, 3H), 1.09 (s, 3H), 0.95 (ddd, J=10.5, 8.6, 5.7, 1H), 0.46 (dd, J=8.6, 4.6, 1H), 0.19 (dd, J=5.7, 4.6, 1H)

$^{13}$C (125 MHz, CDCl$_3$)

147.5(s), 128.3(d), 126.9(d), 126.0(d), 70.8(d), 39.1(d), 34.1(d), 27.5(s), 23.6(q), 20.4(q), 18.9(t), 18.7(q)

Example 5

Synthesis of 1,2-Dimethyl-2-(1-phenylethyl)cyclopropylmethanol

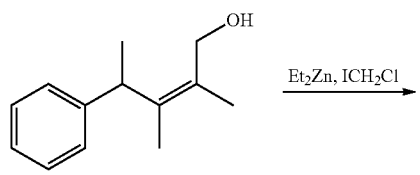

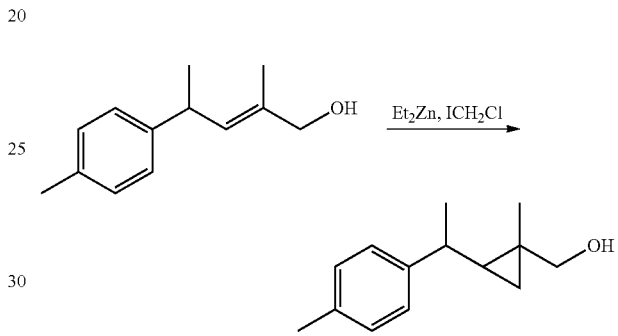

Under a nitrogen atmosphere, a diethylzinc solution in toluene (concentration: 15% by weight, 10.9 g, 13.2 mmol) was placed into a 100-ml flask equipped with a stirring apparatus, a dropping funnel, and a thermometer, and cooled to −15° C. Chloroiodomethane (4.68 g, 26.5 mmol) was placed into the dropping funnel, and added dropwise with the temperature kept between −15 and −20° C. After completion of the dropwise addition, the mixture was stirred at −15° C. for 30 minutes. (Z)-2,3-Dimethyl-4-phenylpent-2-ene-1-ol (1.26 g, 6.63 mmol) was added dropwise at −10 to −15° C. over a period of 20 minutes. After completion of the dropwise addition, the stirring was continued at 12° C. for 60 minutes. Next, a 20% aqueous sulfuric acid solution (4.8 ml) was added. After stirring for 10 minutes, the aqueous layer was separated, and the organic layer was washed twice with water (10 ml). The solvent was recovered under reduced pressure to obtain a condensed residue. This residue was purified by silica gel column chromatography (hexane:ethyl acetate=9:1). [(1S*,2S*)-1,2-Dimethyl-2-((S*)-1-phenylethyl)cyclopropyl]methanol (0.47 g, 2.3 mmol, 35% yield) was obtained as the main isomer, and [(1S*,2S*)-1,2-dimethyl-2-((R*)-1-phenylethyl)cyclopropyl]methanol (0.45 g, 2.2 mmol, 33% yield) was obtained as a minor isomer. The relative configurations of the main isomer and the minor isomer were determined by NOESY measurement.

Main Isomer

GC/MS (m/e):

204 (M$^+$, <1), 186 (3), 171 (25), 149 (45), 132 (39), 131 (79), 117 (86), 115 (36), 106 (44), 105 (100), 99 (37), 91 (60), 77 (31)

$^1$H (500 MHz, CDCl$_3$):

7.32-7.27 (m, 4H), 7.20 (m, 1H), 3.78 (m, 2H), 2.68 (q, 7.2, 1H), 1.36 (d, J=7.2, 3H), 1.35 (OH), 1.25 (s, 3H), 0.92 (s, 3H), 0.73 (d, J=4.8, 1H), 0.22 (d, J=4.8, 1H)

$^{13}$C (125 MHz, CDCl$_3$)

145.1(s), 128.0(d), 127.9(d), 125.9(d), 68.2(t), 42.3(d), 30.2(s), 26.7(s), 25.5(t), 18.3(q), 16.8(q), 14.7(q)

Minor Isomer

GC/MS (m/e):

204 (M$^+$, <1), 186 (3), 171 (24), 149 (44), 132 (46), 131 (89), 117 (94), 115 (38), 106 (48), 105 (100), 99 (38), 91 (65), 77 (35)

$^1$H (500 MHz, CDCl$_3$):

7.32 (ddm, J=7.8, 7.0, 2H), 7.28 (dm, J=7.8, 2H), 7.19 (tm, J=7.0, 1H), 3.64 (m, 2H), 2.64 (q, 7.1, 1H), 1.40 (d, J=7.1, 3H), 1.24 (s, 3H), 1.08 (s, 3H), 0.90 (t, J=6.7, OH), 0.45 (d, J=4.6, 1H), 0.29 (d, J=4.6, 1H)

$^{13}$C (125 MHz, CDCl$_3$)

145.3(s), 128.4(d), 127.5(d), 126.0(d), 68.3(t), 42.5(d), 29.3(s), 28.5(s), 25.1(t), 18.9(q), 18.2(q), 15.6(q)

Example 6

Synthesis of 1-Methyl-2-(1-(4-methylphenyl)ethyl)cyclopropylmethanol

Under a nitrogen atmosphere, a diethylzinc solution in toluene (concentration: 15% by weight, 5.3 g, 6.4 mmol) was placed into a 100-ml flask equipped with a stirring apparatus, a dropping funnel, and a thermometer, and cooled to −20° C. Chloroiodomethane (2.26 g, 12.8 mmol) was placed into the dropping funnel, and added dropwise with the temperature kept between −15 and −20° C. After completion of the dropwise addition, the mixture was stirred at −10 to −15° C. for 10 minutes, and then cooled to −20° C. At the same temperature, (E)-2-methyl-4-(4-methylphenyl)pent-2-en-1-ol (0.60 g, 3.2 mmol) was added dropwise over a period of 10 minutes. After completion of the dropwise addition, the stirring was continued at −15 to −25° C. for 60 minutes. Next, a 20% aqueous sulfuric acid solution (2.5 ml) was added. After stirring for 10 minutes, the aqueous layer was separated, and the organic layer was washed twice with water (10 ml). The solvent was recovered under reduced pressure to obtain a condensed residue. This residue was purified by silica gel column chromatography (hexane:ethyl acetate=9:1). [(1R*,2S*)-1-Methyl-2-((R*)-1-(4-methylphenyl)ethyl)cyclopropyl]methanol (0.24 g, 1.18 mmol, 36% yield) was obtained as the main isomer, and [(1R*,2S*)-1-methyl-2-((S*)-1-(4-methylphenyl)ethyl)cyclopropyl]methanol (0.013 g, 0.064 mmol, 2% yield) was obtained as a minor isomer. The relative configurations of the main isomer and the minor isomer were determined by NOESY measurement.

Main Isomer

GC/MS (m/e):

186 (M$^+$−H$_2$O, 2), 173 (13), 160 (13), 149 (19), 145 (23), 132 (80), 131 (64), 120 (62), 119 (88), 117 (100), 115 (48), 105 (40), 91 (62), 77 (21)

$^1$H (500 MHz, CDCl$_3$):

7.16 (dm, J=8.2, 2H), 7.12 (dm, J=8.2, 2H), 3.41 (d, J=11.0, 1H), 3.35 (d, J=11.0, 1H), 2.33 (s, 3H), 2.27 (dq,

J=10.6, 7.0, 1H), 1.32 (d, J=7.0, 3H), 1.28 (s, 3H), 0.84 (ddd, J=10.6, 8.8, 5.7, 1H), 0.52 (dd, J=8.8, 4.8, 1H), 0.11 (dd, J=5.7, 4.8, 1H)

$^{13}$C (125 MHz, CDCl$_3$)

144.2(s), 135.4(s), 129.0(d), 126.8(d), 72.5(t), 39.4(d), 29.9(d), 23.6(s), 22.7(q), 21.0(q), 16.6(t), 15.3(q)

Minor Isomer

GC/MS (m/e):

204 (M$^+$, <1), 186 (7), 173 (16), 157 (8), 149 (23), 145 (20), 132 (98), 131 (84), 120 (66), 119 (100), 117 (96), 115 (53), 105 (42), 91 (64), 77 (24)

$^1$H (500 MHz, CDCl$_3$):

7.14 (dm, J=8.2, 2H), 7.10 (dm, J=8.2, 2H), 3.34 (d, J=10.8, 1H), 3.27 (d, J=10.8, 1H), 2.32 (s, 3H), 2.31 (dq, J=10.6, 7.0, 1H), 1.33 (d, J=7.0, 3H), 1.06 (s, 3H), 0.95 (ddd, J=10.6, 8.9, 5.6, 1H), 0.68 (dd, J=8.9, 4.7, 1H), 0.18 (dd, J=5.6, 4.7, 1H)

$^{13}$C (125 MHz, CDCl$_3$)

144.6(s), 135.2(s), 129.1(d), 126.4(d), 72.3(t), 39.6(d), 29.3(d), 23.36(q), 23.35(s), 20.9(q), 16.5(t), 15.7(q)

Example 7

Synthesis of 1-Methyl-2-(1-(4-methylphenyl)ethyl)cyclopropylmethanol

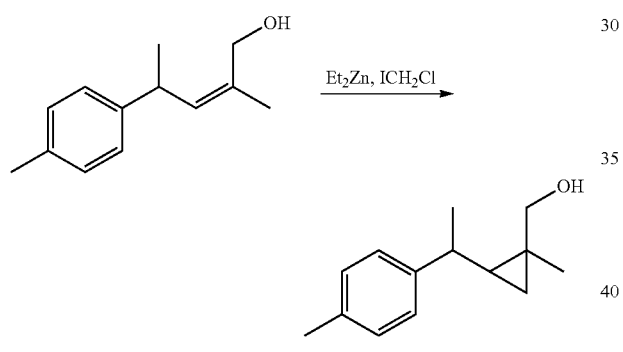

Under a nitrogen atmosphere, a diethylzinc solution in toluene (concentration: 15% by weight, 9.4 g, 11.4 mmol) was placed into a 100-ml flask equipped with a stirring apparatus, a dropping funnel, and a thermometer, and cooled to −15° C. Chloroiodomethane (4.02 g, 22.8 mmol) was placed into the dropping funnel, and added dropwise with the temperature kept at −15° C. After completion of the dropwise addition, the mixture was stirred at −10 to −15° C. for 20 minutes, and then cooled to −25° C. (Z)-2-Methyl-4-(4-methylphenyl)pent-2-en-1-ol (1.08 g, 5.7 mmol) was added dropwise at −20 to −25° C. over a period of 20 minutes. After completion of the dropwise addition, the stirring was continued at −15 to −25° C. for 60 minutes. Next, a 20% aqueous sulfuric acid solution (4.2 ml) was added. After stirring for 10 minutes, the aqueous layer was separated, and the organic layer was washed twice with water (10 ml). The solvent was recovered under reduced pressure to obtain a condensed residue. This residue was purified by silica gel column chromatography (hexane:ethyl acetate=9:1). [(1S*,2S*)-1-Methyl-2-((R*)-1-(4-methylphenyl)ethyl)cyclopropyl]methanol (0.79 g, 3.8 mmol, 68% yield) was obtained as the main isomer, and [(1S*,2S*)-1-methyl-2-((S*)-1-(4-methylphenyl)ethyl)cyclopropyl]methanol (0.21 g, 1.0 mmol, 18% yield) was obtained as a minor isomer. The relative configurations of the main isomer and the minor isomer were determined by NOESY measurement.

Main Isomer

GC/MS (m/e):

186 (M$^+$−H$_2$O, 1), 173 (9), 171 (7), 160 (18), 149 (16), 145 (25), 132 (76), 131 (66), 120 (65), 119 (82), 117 (100), 115 (47), 105 (46), 91 (56), 77 (19)

$^1$H (500 MHz, CDCl$_3$):

7.14 (dm, J=8.3, 2H), 7.12 (dm, J=8.3, 2H), 3.71 (d, J=11.3, 1H), 3.69 (d, J=11.3, 1H), 2.32 (s, 3H), 2.32 (dq, J=10.6, 6.9, 1H), 1.36 (d, J=6.9, 3H), 1.29 (br.s, OH), 1.20 (s, 3H), 0.92 (ddd, J=10.6, 8.4, 5.8, 1H), 0.44 (dd, J=8.4, 4.8, 1H), 0.20 (dd, J=5.8, 4.8, 1H)

$^{13}$C (125 MHz, CDCl$_3$)

144.3(s), 135.4(s), 129.0(d), 126.7(d), 67.1(t), 39.6(d), 33.4(d), 23.5(s), 23.1(q), 22.9(q), 21.0(q), 17.3(t)

Minor Isomer

GC/MS (m/e):

186 (M$^+$−H$_2$O, 9), 173 (11), 171 (15), 157 (10), 149 (19), 145 (20), 132 (91), 131 (90), 120 (70), 119 (95), 117 (100), 115 (54), 105 (43), 91 (66), 77 (23)

$^1$H (500 MHz, CDCl$_3$):

7.17 (dm, J=8.2, 2H), 7.13 (dm, J=8.2, 2H), 3.54 (dd, J=12.6, 9.7, 1H), 3.33 (dd, J=12.6, 1.2, 1H), 2.31 (s, 3H), 2.30 (dq, J=10.6, 6.9, 1H), 1.32 (d, J=6.9, 3H), 1.13 (s, 3H), 1.03 (ddd, J=10.6, 8.3, 5.4, 1H), 0.64 (dd, J=8.3, 4.6, 1H), 0.39 (br.d, J=9, 7, OH), 0.25 (dd, J=5.4, 4.6, 1H)

$^{13}$C (125 MHz, CDCl$_3$)

144.7(s), 135.9(s), 129.5(d), 126.3(d), 67.4(t), 40.5(d), 32.0(d), 24.2(q), 23.1(s), 22.6(q), 21.0(q), 17.9(t)

Example 8

Synthesis of 1-Methyl-2-(1-(3-methylphenyl)ethyl)cyclopropylmethanol

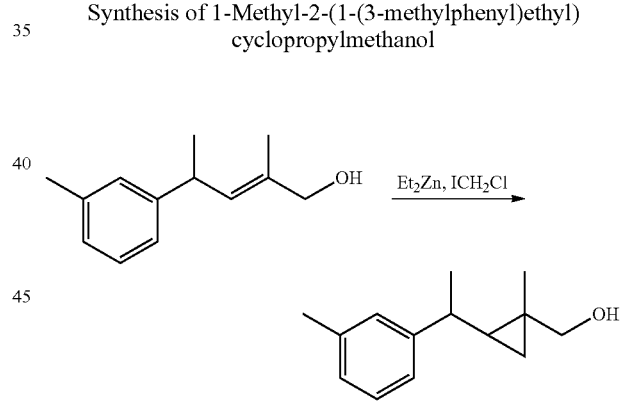

Under a nitrogen atmosphere, a diethylzinc solution in toluene (concentration: 15% by weight, 6.92 g, 8.4 mmol) was placed into a 100-ml flask equipped with a stirring apparatus, a dropping funnel, and a thermometer, and cooled to −25° C. Chloroiodomethane (2.96 g, 16.8 mmol) was placed into the dropping funnel, and added dropwise with the temperature kept between −20 and −25° C. After completion of the dropwise addition, the mixture was stirred at −10 to −20° C. for 15 minutes, and then cooled to −25° C. At the same temperature, (E)-2-methyl-4-(3-methylphenyl)pent-2-en-1-ol (0.80 g, 4.2 mmol) was added dropwise over a period of 20 minutes. After completion of the dropwise addition, the stirring was continued at −10 to −25° C. for 20 minutes. Next, a 20% aqueous sulfuric acid solution (3.1 ml) was added. After stirring for 10 minutes, the aqueous layer was separated, and the organic layer was washed twice with water (10 ml). The solvent was recovered under reduced pressure to obtain a condensed residue. This residue was purified by silica gel column chromatography (hexane:ethyl acetate=9:1). [(1R*,2S*)-1-Methyl-2-((R*)-1-(3-methylphenyl)ethyl)cyclopropyl]methanol (0.38 g, 1.9 mmol, 45% yield) was obtained as the main isomer, and [(1R*,2S*)-1-methyl-2-((S*)-1-(3-methylphenyl)ethyl)cyclopropyl]methanol (0.014 g, 0.069 mmol, yield 1.6%) was obtained as a minor isomer. The relative configurations of the main isomer and the minor isomer were determined by NOESY measurement.

Main Isomer

GC/MS (m/e):

186 ($M^+$–$H_2O$, 1), 173 (16), 160 (15), 145 (30), 132 (81), 131 (66), 120 (73), 119 (81), 117 (100), 115 (46), 105 (36), 91 (49), 77 (16)

$^1$H (500 MHz, $CDCl_3$):

7.19 (dd, J=8.0, 7.4, 1H), 7.07 (br.s, 1H), 7.06 (dm, 8.0, 1H), 7.02 (dm, 7.4, 1H), 3.42 (d, J=11.0, 1H), 3.36 (d, J=11.0, 1H), 2.35 (s, 3H), 2.26 (dq, J=10.6, 7.0, 1H), 1.33 (d, J=7.0, 3H), 1.28 (s, 3H), 0.86 (ddd, J=10.6, 8.8, 5.7, 1H), 0.52 (dd, J=8.8, 4.8, 1H), 0.12 (dd, J=5.7, 4.8, 1H)

$^{13}$C (125 MHz, $CDCl_3$)

147.2(s), 137.8(s), 128.2(d), 127.7(d), 126.7(d), 124.0(d), 72.4(t), 39.7(d), 29.7(d), 23.6(s), 22.7(q), 21.5(q), 16.6(t), 15.3(q)

Minor Isomer

GC/MS (m/e):

204 ($M^+$, <1), 186 (4), 173 (17), 157 (10), 149 (11), 145 (21), 132 (93), 131 (80), 120 (79), 119 (88), 117 (100), 115 (54), 105 (42), 91 (71), 77 (26)

$^1$H (500 MHz, $CDCl_3$):

7.18 (ddm, J=8.4, 7.4, 1H), 7.06 (br.s, 1H), 7.05 (dm, 8.4, 1H), 6.99 (dm, 7.4, 1H), 3.33 (d, J=10.9, 1H), 3.27 (d, J=10.9, 1H), 2.33 (s, 3H), 2.30 (dq, J=10.5, 7.0, 1H), 1.34 (d, J=7.0, 3H), 1.09 (br.s, OH), 1.06 (s, 3H), 0.96 (ddd, J=10.5, 8.9, 5.5, 1H), 0.68 (dd, J=8.9, 4.7, 1H), 0.17 (dd, J=5.5, 4.7, 1H)

$^{13}$C (125 MHz, $CDCl_3$)

147.6(s), 137.8(s), 128.3(d), 127.4(d), 126.6(d), 123.6(d), 72.2(t), 39.9(d), 29.2(d), 23.34(s), 23.28(q), 21.5(q), 16.5(t), 15.7(q)

Example 9

Synthesis of 1-methyl-2-(1-(3-methylphenyl)ethyl)cyclopropylmethanol

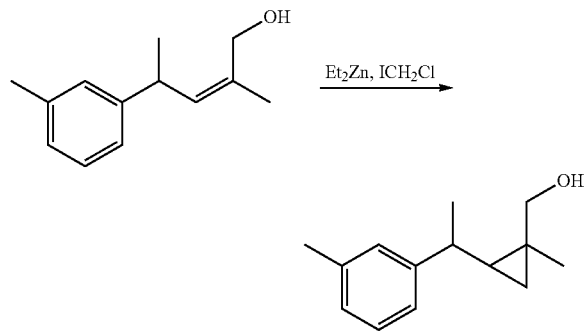

Under a nitrogen atmosphere, a diethylzinc solution in toluene (concentration: 15% by weight, 9.4 g, 0.0114 mol) was placed into a 100-ml flask equipped with a stirring apparatus, a dropping funnel, and a thermometer, and cooled to −15° C. Chloroiodomethane (4.02 g, 22.8 mmol) was placed into the dropping funnel, and added dropwise with the temperature kept between −15 and −20° C. After completion of the dropwise addition, the mixture was stirred at −10 to −15° C. for 20 minutes, and then cooled to −25° C. (Z)-2-Methyl-4-(3-methylphenyl)pent-2-en-1-ol (1.09 g, 5.7 mmol) was added dropwise at −20 to −25° C. over a period of 20 minutes. After completion of the dropwise addition, the stirring was continued at −15 to −25° C. for 40 minutes. Next, a 20% aqueous sulfuric acid solution (4.2 ml) was added. After stirring for 10 minutes, the aqueous layer was separated, and the organic layer was washed twice with water (10 ml). The solvent was recovered under reduced pressure to obtain a condensed residue. This residue was purified by silica gel column chromatography (hexane:ethyl acetate=9:1). [(1S*,2S*)-1-Methyl-2-((R*)-1-(3-methylphenyl)ethyl)cyclopropyl]methanol (0.83 g, 4.1 mmol, 70% yield) was obtained as the main isomer, and [(1S*,2S*)-1-methyl-2-((S*)-1-(3-methylphenyl)ethyl)cyclopropyl]methanol (0.20 g, 0.99 mmol, 17% yield) was obtained as a minor isomer. The relative configurations of the main isomer and the minor isomer were determined by NOESY measurement.

Main Isomer

GC/MS (m/e):

186 ($M^+$–$H_2O$, 1), 171 (7), 160 (20), 145 (30), 132 (66), 131 (65), 120 (69), 119 (71), 117 (100), 115 (50), 105 (46), 91 (62), 77 (21)

$^1$H (500 MHz, $CDCl_3$):

7.19 (dt, J=0.9, 7.4, 1H), 7.05 (s, 1H), 7.04 (dm, J=7.4, 1H), 7.01 (dm, J=7.4, 1H), 3.71 (d, J=11.3, 1H), 3.68 (d, J=11.3, 1H), 2.34 (s, 3H), 2.32 (dq, J=10.6, 7.0, 1H), 1.36 (d, J=7.0, 3H), 1.31 (br.s, OH), 1.20 (s, 3H), 0.93 (ddd, J=10.6, 8.4, 5.8, 1H), 0.44 (dd, J=8.4, 4.8, 1H), 0.21 (dd, J=5.8, 4.8, 1H)

$^{13}$C (125 MHz, $CDCl_3$)

147.3(s), 137.8(s), 128.2(d), 127.7(d), 126.7(d), 123.9(d), 67.1(t), 40.0(d), 33.3(d), 23.5(s), 23.1(q), 22.9(q), 21.5(q), 17.3(t)

Minor Isomer

GC/MS (m/e):

186 ($M^+$–$H_2O$, 7), 171 (18), 157 (11), 145 (22), 132 (81), 131 (95), 120 (77), 119 (83), 117 (100), 115 (63), 105 (45), 91 (76), 77 (25)

$^1$H (500 MHz, $CDCl_3$):

7.21 (dd, J=8, 7, 1H), 7.08 (dm, J=7, 1H), 7.07 (m, 1H), 7.02 (dm, J=8, 1H), 3.53 (dd, J=11.7, 10.0, 1H), 3.34 (dd, J=11.7, 2.8, 1H), 2.34 (s, 3H), 2.30 (dq, J=10.6, 6.9, 1H), 1.33 (d, J=6.9, 3H), 1.13 (s, 3H), 1.04 (ddd, J=10.6, 8.3, 5.4, 1H), 0.64 (dd, J=8.3, 4.6, 1H), 0.42 (dd, J=10.0, 2.8, OH), 0.26 (dd, J=5.4, 4.6, 1H)

$^{13}$C (125 MHz, $CDCl_3$)

147.7(s), 138.4(s), 128.7(d), 127.3(d), 127.2(d), 123.4(d), 67.4(t), 40.8(d), 31.9(d), 24.1(q), 23.1(s), 22.6(q), 21.5(q), 17.9(t)

Example 10

Synthesis of 1-Methyl-2-(1-(2-methylphenyl)ethyl)cyclopropylmethanol

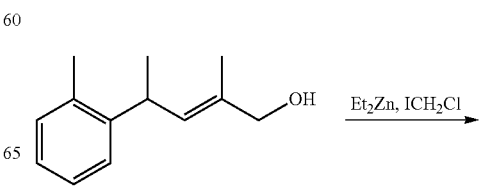

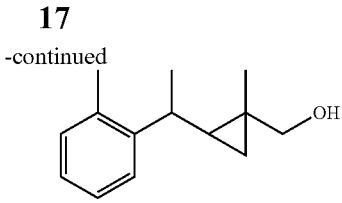

Under a nitrogen atmosphere, a diethylzinc solution in toluene (concentration: 15% by weight, 6.92 g, 8.4 mmol) was placed into a 100-ml flask equipped with a stirring apparatus, a dropping funnel, and a thermometer, and cooled to −20° C. Chloroiodomethane (2.96 g, 16.8 mmol) was placed into the dropping funnel, and added dropwise with the temperature kept between −15 and −20° C. After completion of the dropwise addition, the mixture was stirred at −5 to −15° C. for 10 minutes, and then cooled to −25° C. (E)-2-Methyl-4-(2-methylphenyl)pent-2-en-1-ol (0.80 g, 4.2 mmol) was added dropwise at −20 to −25° C. over a period of 20 minutes. After completion of the dropwise addition, the stirring was continued at −15 to −25° C. for 60 minutes. Next, a 20% aqueous sulfuric acid solution (3.1 ml) was added. After stirring for 10 minutes, the aqueous layer was separated, and the organic layer was washed twice with water (10 ml). The solvent was recovered under reduced pressure to obtain a condensed residue. This residue was purified by silica gel column chromatography (hexane:ethyl acetate=9:1). [(1R*, 2S*)-1-Methyl-2-((R*)-1-(2-methylphenyl)ethyl)cyclopropyl]methanol (0.32 g, 1.6 mmol, 37% yield) was obtained as the main isomer, and [(1R*,2S*)-1-methyl-2-((S*)-1-(2-methylphenyl)ethyl)cyclopropyl]methanol (0.025 g, 0.12 mmol, 3% yield) was obtained as a minor isomer. The relative configurations of the main isomer and the minor isomer were determined by NOESY measurement.

Main Isomer

GC/MS (m/e):

204 (M+, <1), 186 (5), 171 (13), 157 (10), 149 (10), 145 (15), 143 (20), 132 (64), 131 (63), 120 (74), 119 (87), 117 (100), 115 (53), 105 (35), 91 (56), 77 (18)

$^1$H (500 MHz, CDCl$_3$):

7.36 (dd, J=7.7, 1.0, 1H), 7.19 (tm, J=7.7, 1H), 7.13 (dm, J=7.7, 1H), 7.09 (dt, J=1.4, 7.7, 1H), 3.45 (d, J=11.0, 1H), 3.38 (d, J=11.0, 1H), 2.62 (dq, J=10.5, 6.9, 1H), 2.31 (s, 3H), 1.30 (s, 3H), 1.27 (d, J=6.9, 3H), 0.99 (ddd, J=10.5, 8.9, 5.8, 1H), 0.51 (dd, J=8.9, 4.9, 1H), 0.02 (dd, J=5.8, 4.9, 1H)

$^{13}$C (125 MHz, CDCl$_3$)

145.6(s), 134.7(s), 130.2(d), 126.2(d), 126.1(d), 125.6(d), 72.5(t), 34.6(d), 29.1(d), 23.6(s), 22.9(q), 19.6(q), 16.5(t), 15.5(q)

Minor Isomer

GC/MS (m/e):

186 (M+−H$_2$O, 6), 173 (17), 171 (15), 157 (14), 149 (17), 143 (25), 132 (62), 131 (70), 129 (30), 128 (40), 120 (52), 119 (72), 117 (100), 115 (66), 105 (32), 91 (60), 77 (23)

$^1$H (500 MHz, CDCl$_3$):

7.33 (dd, J=7.5, 0.8, 1H), 7.19 (dt, J=2.0, 7.5, 1H), 7.11 (dm, J=7.5, 1H), 7.08 (dt, J=1.4, 7.5, 1H), 3.35 (d, J=10.8, 1H), 3.31 (d, J=10.8, 1H), 2.48 (dq, J=10.4, 6.9, 1H), 2.29 (s, 3H), 1.27 (d, J=6.9, 3H), 1.15 (ddd, J=10.4, 8.8, 5.4, 1H), 1.09 (br.s), 0.90 (s, 3H), 0.74 (dd, J=8.8, 4.6, 1H), 0.22 (dd, J=5.4, 4.6, 1H)

$^{13}$C (125 MHz, CDCl$_3$)

146.2(s), 134.4(s), 130.2(d), 126.3(d), 125.6(d), 125.2(d), 72.2(t), 36.3(d), 28.5(d), 23.0(s), 22.9(q), 19.2(q), 17.3(t), 15.5(q)

Example 11

Synthesis of 1-Methyl-2-(1-(2-methylphenyl)ethyl)cyclopropylmethanol

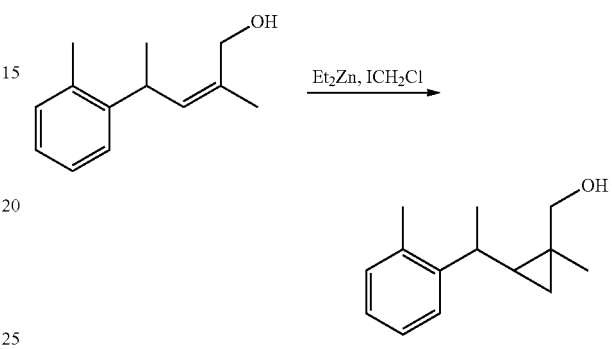

Under a nitrogen atmosphere, a diethylzinc solution in toluene (concentration: 15% by weight, 5.4 g, 0.0066 mol) was placed into a 100-ml flask equipped with a stirring apparatus, a dropping funnel, and a thermometer, and cooled to −20° C. Chloroiodomethane (2.33 g, 13.2 mmol) was placed into the dropping funnel, and added dropwise with the temperature kept between −15 and −20° C. After completion of the dropwise addition, the mixture was stirred at −5 to −15° C. for 20 minutes, and then cooled to −25° C. (Z)-2-Methyl-4-(2-methylphenyl)pent-2-en-1-ol (0.62 g, 3.3 mmol) was added dropwise at −20 to −25° C. over a period of 15 minutes. After completion of the dropwise addition, the stirring was continued at −15 to −25° C. for 20 minutes. Next, a 20% aqueous sulfuric acid solution (2.5 ml) was added. After stirring for 10 minutes, the aqueous layer was separated, and the organic layer was washed twice with water (10 ml). The solvent was recovered under reduced pressure to obtain a condensed residue. This residue was purified by silica gel column chromatography (hexane:ethyl acetate=9:1). [(1S*, 2S*)-1-Methyl-2-((R*)-1-(2-methylphenyl)ethyl)cyclopropyl]methanol (0.47 g, 2.3 mmol, 70% yield) was obtained as the main isomer, and [(1S*,2S*)-1-methyl-2-((S*)-1-(2-methylphenyl)ethyl)cyclopropyl]methanol (0.12 g, 0.59 mmol, 17% yield) was obtained as a minor isomer. The relative configurations of the main isomer and the minor isomer were determined by NOESY measurement.

Main Isomer

GC/MS (m/e):

186 (M+−H$_2$O, <1), 173 (4), 171 (6), 160 (8), 149 (9), 145 (18), 143 (15), 132 (55), 131 (62), 120 (76), 119 (77), 117 (100), 115 (56), 105 (38), 91 (59), 77 (19)

$^1$H (500 MHz, CDCl$_3$):

7.35 (dd, J=7, 1.1, 1H), 7.19 (dt, J=1.8, 7, 1H), 7.12 (dd, J=7, 1.8, 1H), 7.08 (dt, J=1.3, 7, 1H), 3.725 (d, J=11.5, 1H), 3.715 (d, J=11.5, 1H), 2.67 (dq, J=10.5, 6.9, 1H), 2.29 (s, 3H), 1.32 (d, J=6.9, 3H), 1.23 (s, 3H), 1.06 (ddd, J=10.5, 8.4, 5.9, 1H), 0.43 (dd, J=8.4, 4.8, 1H), 0.11 (dd, J=5.9, 4.8, 1H)

$^{13}$C (125 MHz, CDCl$_3$)

145.8(s), 134.7(s), 130.2(d), 126.2(d), 126.1(d), 125.6(d), 67.3(t), 34.8(d), 32.6(d), 23.5(s), 23.2(q), 23.0(q), 19.6(q), 17.1(t)

Minor Isomer
GC/MS (m/e):
186 (M+–H$_2$O, 2), 173 (12), 171 (8), 157 (8), 149 (14), 145 (14), 143 (17), 132 (69), 131 (73), 120 (64), 119 (67), 117 (100), 115 (64), 105 (36), 91 (73), 77 (22)
$^1$H (500 MHz, CDCl$_3$):
7.41 (dd, J=7, 0.9, 1H), 7.22 (dt, J=2.2, 7, 1H), 7.13 (dm, J=7, 1H), 7.11 (dt, J=1.3, 7, 1H), 3.47 (dd, J=11.7, 9, 1H), 3.17 (d, J=11.7, 1H), 2.52 (dq, J=10.4, 6.8, 1H), 2.30 (s, 3H), 1.28 (d, J=6.8, 3H), 1.18 (ddd, J=10.4, 8.2, 5.4, 1H), 1.15 (s, 3H), 0.70 (dd, J=8.2, 4.2, 1H), 0.29 (dd, J=5.4, 4.2, 1H), 0.17 (br.d, J=9, OH)
$^{13}$C (125 MHz, CDCl$_3$)
145.8(s), 134.6(s), 130.6(d), 126.7(d), 126.2(d), 125.4(d), 67.6(t), 37.0(d), 31.5(d), 22.91(s), 22.88(q), 22.5(q), 19.1(q), 18.6(t)

Example 12

Synthesis of 2-[(1R*,2S*)-1-Methyl-2-(1-phenylethyl)cyclopropyl]acetaldehyde

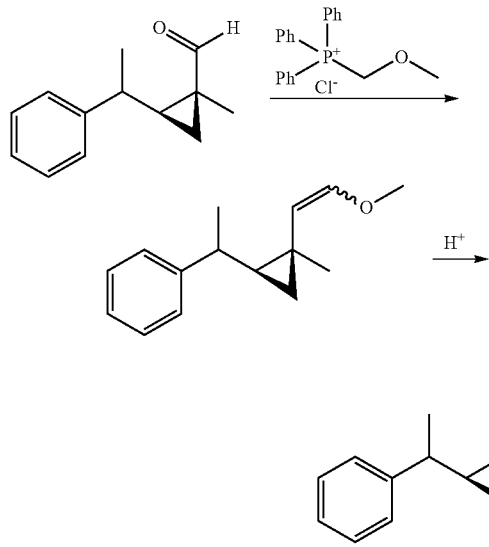

Under a nitrogen atmosphere, (methoxymethyl)triphenylphosphonium chloride (5.0 g, 14.6 mmol) and tetrahydrofuran (20 ml) were placed into a 200-ml flask equipped with a stirring apparatus, a dropping funnel, and a thermometer, and cooled to −40° C. A solution of potassium t-butoxide (1.63 g, 14.5 mmol) in tetrahydrofuran (10 ml) was placed into the dropping funnel, and added dropwise with the temperature kept between −35 and −40° C. After completion of the dropwise addition, the mixture was stirred at the same temperature for 5 minutes, and then (1S*,2S*)-1-methyl-2-(1-phenylethyl)cyclopropane carbaldehyde (1.5 g, 8.0 mmol, a diastereomer mixture with a component ratio of 1:2) was added dropwise over a period of 5 minutes. After completion of the dropwise addition, the temperature was raised to −20° C., and the stirring was continued for 2 hours. Next, a saturated aqueous ammonium chloride solution (20 ml) and hexane (30 ml) were added. After stirring for 10 minutes, the aqueous layer was separated, and the organic layer was washed twice with water (10 ml). The solvent was recovered under reduced pressure. The precipitated white solid was filtered to obtain the residue. Next, under a nitrogen atmosphere, the residue (1.33 g) obtained as above, acetonitrile (6 ml), and a 5% aqueous sulfuric acid solution (2 ml) were placed into a 100-ml flask equipped with a stirring apparatus, a reflux tube, and a thermometer, and starred at 55° C. for 1 hour. After that, toluene (10 ml) was added, the aqueous layer was separated, and the organic layer was washed with water. The solvent was recovered under reduced pressure to obtain a condensed residue. This residue was purified by silica gel column chromatography (hexane:ethyl acetate=8:2) to obtain 2-[(1R*,2S*)-1-methyl-2-(1-phenylethyl)cyclopropyl]acetaldehyde (a diastereomer mixture, 0.56 g, 2.8 mmol, 35% yield).

Main Isomer
GC/MS (m/e):
202 (M+, <1), 187 (<1), 169 (1), 158 (9), 143 (14), 128 (11), 118 (100), 117 (85), 105 (90), 97 (56), 91 (36), 77 (22)
Minor Isomer
GC/MS (m/e):
202 (M+, <1), 187 (<1), 169 (1), 158 (9), 143 (16), 128 (11), 118 (99), 117 (76), 105 (100), 97 (51), 91 (39), 77 (23)
$^{13}$C (125 MHz, CDCl$_3$): data of mixture
203.5(d), 203.1(d), 146.9(s), 146.8(s), 128.5(d), 128.4(d), 126.9(d), 126.6(d), 126.1(d), 48.0(t), 47.9(t), 41.4(d), 40.6 (d), 31.7(d), 30.6(d), 25.5(q), 25.2(q), 23.8(q), 22.5(q), 18.6(t), 18.3(t), 17.1(s), 16.7(s)

Example 13

Synthesis of 2-[(1R*,2S*)-1-Methyl-2-(1-phenylethyl)cyclopropyl]ethanol

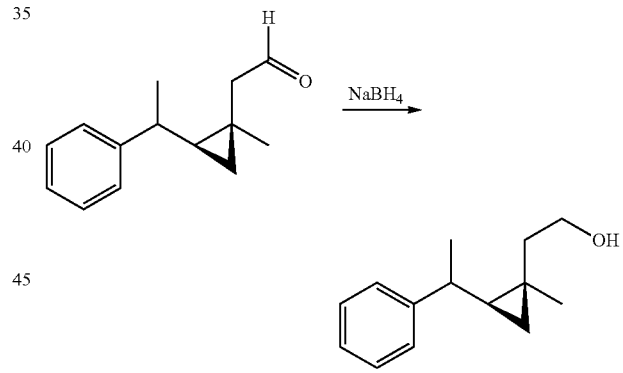

under a nitrogen atmosphere, 2-[(1R*,2S*)-1-methyl-2-(1-phenylethyl)cyclopropyl]acetaldehyde (a diastereomer mixture with a component ratio of 1:2, 0.20 g, 0.99 mmol), cyclopentyl methyl ether (4 ml), and sodium borohydride (0.05 g, 1.3 mmol) were placed into a 30-ml flask equipped with a stirring apparatus, a dropping funnel, and a thermometer, and methanol (0.05 g) was added with stirring at 20° C., followed by stirring at the same temperature for 60 minutes. Next, a 5% aqueous sulfuric acid solution (1.3 g) was added. After stirring for 10 minutes, the aqueous layer was separated, and the organic layer was washed twice with water (2 ml). The solvent was recovered under reduced pressure to obtain a condensed residue. This residue was purified by silica gel column chromatography (hexane:ethyl acetate=8:2) to obtain 2-[(1R*,2S*)-1-methyl-2-(1-phenylethyl)cyclopropyl]ethanol (a diastereomer mixture with a component ratio of 1:2, 0.19 g, 0.93 mmol, 94% yield).

Main Isomer

GC/MS (m/e):

204 (M+, <1), 189 (<1), 171 (1), 159 (7), 143 (6), 131 (23), 118 (100), 117 (51), 105 (87), 91 (28), 77 (15) Minor Isomer GC/MS (m/e):

204 (M+, <1), 189 (<1), 171 (2), 159 (10), 143 (8), 131 (27), 118 (92), 117 (47), 105 (100), 91 (30), 77 (16)

$^{13}$C (125 MHz, CDCl$_3$): data of mixture 147.7(s), 147.5(s), 128.29(d), 128.26(d), 126.9(d), 126.7 (d), 125.9(d), 125.8(d), 61.7(t), 61.5(t), 40.5(d), 40.1(d), 36.6 (t), 36.4(t), 32.6(d), 31.3(d), 25.1(q), 24.7(q), 23.8(q), 22.6 (q), 18.5(t), 18.33(t), 18.30(s), 18.0(s)

Example 14

Synthesis of 1-[(1R*,2S*)-1-Methyl-2-(1-phenyl-ethyl)cyclopropyl]propan-2-ol

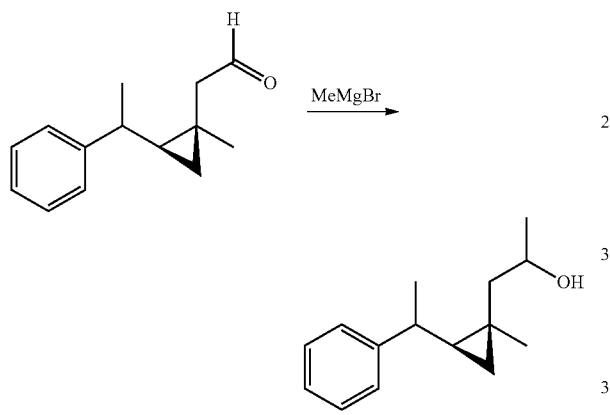

Under a nitrogen atmosphere, methyl magnesium bromide (0.97 mol/L tetrahydrofuran solution, 3.0 ml, 2.9 mmol) was placed into a 30-ml flask equipped with a stirring apparatus, a dropping funnel, and a thermometer. In the dropping funnel, 2-[(1R*,2S*)-1-methyl-2-(1-phenylethyl)cyclopropyl]ac-etaldehyde (a diastereomer mixture with a component ratio of 1:2, 0.20 g, 0.99 mmol) and tetrahydrofuran (1 ml) were placed, and added dropwise in 5 minutes, with the temperature kept at 20° C. At the same temperature, the mixture was stirred for 30 minutes. Next, a 5% aqueous sulfuric acid solution (2.9 g) was added. After stirring for 10 minutes, the aqueous layer was separated, and the organic layer was washed twice with water (2 ml). The solvent was recovered under reduced pressure to obtain a condensed residue. The results of a GC analysis showed that the condensed residue was a mixture of four isomers. This residue was purified by silica gel column chromatography (hexane:ethyl acetate=8:2). Thus, a component (0.016 g, 0.07 mmol, 7% yield) with the longest retention time in the GC analysis was obtained. Results of evaluation based on gas chromatography-olfactometry (GC-O) showed that this component was a component having the lowest odor threshold, among the 4 isomers.

GC/MS (m/e):

218 (M+, <1), 200 (1), 185 (3), 171 (4), 157 (8), 143 (16), 131 (13), 118 (100), 117 (50), 105 (90), 91 (35), 77 (14), 69 (18)

$^1$H (500 MHz, CDCl$_3$):

7.29 (ddm, J=7.5, 7.2, 2H), 7.25 (dm, J=7.5, 2H), 7.19 (tm, J=7.2, 1H), 4.09 (m, 1H), 2.29 (dq, J=10.5, 6.9, 1H), 2.03 (ddd, J=13.6, 5.9, 1.3, 1H), 1.42 (br.s, OH), 1.33 (d, J=6.9, 3H), 1.28 (d, 6.2, 3H), 1.27 (dd, J=13.6, 7.7, 1H), 1.11 (s, 3H), 0.71 (ddd, J=10.5, 8.6, 5.8, 1H), 0.44 (ddd, J=8.6, 4.7, 1.3, 1H), 0.01 (dd, J=5.8, 4.7, 1H)

$^{13}$C (125 MHz, CDCl$_3$)

147.6(s), 128.3(d), 127.0(d), 125.8(d), 67.6(d), 42.7(t), 40.0(d), 32.9(d), 25.7(q), 23.5(q), 22.5(q), 18.95(s), 18.90(t)

Example 15

Synthesis of 2-[(1S*,2S*)-1-Methyl-2-((R*)1-phe-nylethyl)cyclopropyl]ethanol

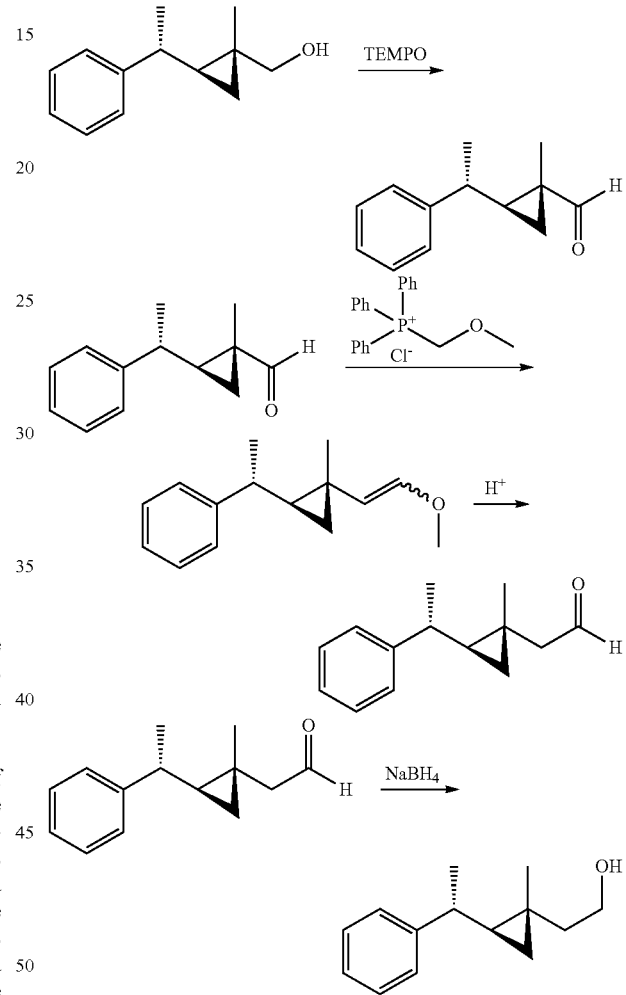

(1R*,2S*)-1-Methyl-2-[(R*)-1-phenylethyl]cyclopropane carbaldehyde was obtained by changing the raw material in the above-described method of Example 3 to 2-[(1R*,2S*)-1-methyl-2-((R*)1-phenylethyl)cyclopropyl]methanol (2.04 g, 10.7 mmol), and carrying out the same method as in Example 3. Subsequently, 2-[(1S*,2S*)-1-methyl-2-((R*)1-phenylethyl)cyclopropyl]acetaldehyde (1.26 g, 6.2 mmol) was obtained by the same method as in Example 12 described above. Moreover, 2-[(1S*,2S*)-1-methyl-2-((R*)1-phenylethyl)cyclopropyl]ethanol (1.21 g, 5.9 mmol) was obtained by the same method as in Example 13 described above. The total yield was 55%.

GC/MS (m/e):

204 (M+, <1), 189 (<1), 171 (1), 159 (8), 143 (7), 131 (22), 118 (100), 117 (52), 105 (87), 91 (28), 77 (15), $^1$H (500 MHz, CDCl$_3$):

7.30 (ddm, J=8.3, 7.1, 2H), 7.26 (dm, J=8.3, 2H), 7.19 (tm, J=7.1, 1H), 3.80 (m, 2H), 2.28 (dq, J=10.7.0, 1H), 1.68 (ddd, J=13.8, 7.6, 6.5, 1H), 1.42 (ddd, J=, 13.8, 7.7, 6.7, 1H), 1.34 (d, J=7.0, 3H), 1.27 (m, OH), 1.20 (s, 3H), 0.78 (ddd, J=10.6, 8.7, 5.7, 1H), 0.45 (dd, J=8.7, 4.7, 1H), 0.06 (dd, J=5.7, 4.7, 1H)

$^{13}$C (125 MHz, CDCl$_3$)

147.4(s), 128.3(d), 126.9(d), 125.9(d), 61.4(t), 44.2(t), 40.1(d), 31.4(d), 22.6(q), 19.0(t), 18.1(s), 17.5(q)

(Evaluation of Odor Quality)

The compounds synthesized in Examples 1 to 15 described above were evaluated for the quality of their odors. The results are shown in the following Tables 1 to 3 separately according to the odor quality.

TABLE 1

| | Structural formula | Quality of odor |
| --- | --- | --- |
| Example 1 | | Floral, Rose, Muguet, 3-Methyl-5-phenyl-1-pentanol like, Strong |
| Example 6 | | Floral, Rose, Muguet |
| Example 8 | | Floral, Rose, Muguet, Strong |
| Example 10 | | Floral, Rose, Muguet |
| Example 15 | | Floral, Rose, Muguet |

TABLE 2

| | Structural formula | Odor quality |
| --- | --- | --- |
| Example 2 | | Citrus, Rhubarb, Woody, Strong |
| Example 4 | | Citrus, Rhubarb, Animal, Strong |
| Example 5 | | Citrus, Rhubarb, Strong |
| Example 7 | | Citrus, Rhubarb |
| Example 9 | | Citrus, Rhubarb, Strong |
| Example 11 | | Citrus, Rhubarb, Strong |
| Example 13 Isomer with long GC retention time | | Citrus, Rhubarb |
| Example 14 | | Citrus, Rhubarb |

TABLE 3

| | Structural formula | Odor quality |
| --- | --- | --- |
| Example 3 | | Aldehyde-like, Floral, Citrus |

TABLE 3-continued

| | Structural formula | Odor quality |
|---|---|---|
| Example 12 | (structure) | Aldehyde-like, Floral, Citrus, weak |

Example 16

Flavor and/or Fragrance Composition with Muguet Note

Flavor and/or fragrance compositions for perfume were prepared according to the formulation shown in Table 4 below by using the compounds synthesized in Examples 1, 2, 4, 8, 9, and 10 described above.

TABLE 4

| Formulation | Parts by weight |
|---|---|
| Amyl cinnamic aldehyde | 50 |
| Benzyl acetate | 50 |
| l-Citronellol | 3 |
| Citronellol | 100 |
| Dihydromyrcenol | 30 |
| Dimethyl phenylethyl carbinol | 50 |
| Hexyl cinnamic aldehyde | 100 |
| Indole | 2 |
| Linalool | 100 |
| Phenylacetaldehyde dimethyl acetal | 10 |
| Phenylethyl alcohol | 150 |
| SANTALEX T ® (manufactured by Takasago International Corporation) | 25 |
| Terpineol | 30 |
| Compound of Example 1, 2, 4, 8, 9, or 10 | 300 |
| Total | 1000 |

Results of sensory evaluation conducted by four professional panelists with five or more year experience were as follows. Specifically, all the panelists stated that the flavor and/or fragrance compositions with muguet note containing the compounds of Examples 1, 2, 4, 8, 9, and 10 had strong floral odors, and also had excellent diffusibility.

Example 17

Flavor and/or Fragrance Compositions with Marine Note

Flavor and/or fragrance compositions for perfume were prepared according to the formulation shown in Table 5 below by using the compounds of Examples 1, 2, 4, 8, 9, and 10.

TABLE 5

| Formulation | Parts by weight |
|---|---|
| CALONE ® (manufactured by Firmenich) | 10 |
| Canthoxal | 10 |
| γ-Decalactone | 30 |
| β-Dihydroionone | 50 |
| Eugenol | 5 |
| HEDIONE ® (manufactured by Firmenich) | 250 |
| HELIOBOUQUET ® (manufactured by Takasago International Corporation) | 40 |
| cis-3-Hexenyl salicylate | 15 |
| l-Citronellol | 40 |
| Linalool | 50 |
| l-Muscone (manufactured by Takasago International Corporation) | 40 |
| MUSK T ® (manufactured by Takasago International Corporation) | 200 |
| ORBITONE ® (manufactured by Takasago International Corporation) | 150 |
| THESARON ® (manufactured by Takasago International Corporation) | 10 |
| Compound of Example 1, 2, 4, 8, 9, or 10 | 100 |
| Total | 1000 |

Results of sensory evaluation conducted by four professional panelists with five or more year experience were as follows. Specifically, all the panelists stated that the flavor and/or fragrance compositions with marine note containing the compounds of Examples 1, 2, 4, 8, 9, and 10 had distinct marine and ozone notes, and also had excellent diffusibility.

Example 18

Shampoo

Shampoos (100 g) each scented with 1.0% of one of the flavor and/or fragrance compositions of Examples 16 and Example 17 were prepared according to the formulation shown in Table 6 below.

TABLE 6

| Formulation (components) | Blended amount (g) |
|---|---|
| Sodium polyoxyethylene lauryl ether sulfate | 14.00 |
| Lauramidopropyl betaine | 4.00 |
| Coconut oil fatty acid diethanol amide | 3.00 |
| Cationic cellulose | 0.50 |
| Ethylene glycol distearate | 1.00 |
| ethyl paraoxybenzoate | 0.25 |
| Citric acid | Quantum Sufficient |
| Flavor and/or fragrance composition of Example 16 or 17 | 1.00 |
| Purified water | the Balance |
| Total | 100.00 |

The invention claimed is:

1. A compound represented by Formula (1):

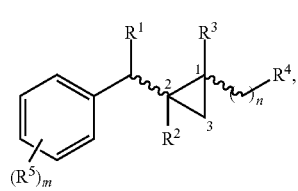

wherein
- $R^1$, $R^2$, $R^3$, and $R^5$ each represent a hydrogen atom or an alkyl group having 1 to 3 carbon atoms, provided that two or more groups of $R^1$, $R^2$, $R^3$, and $R^5$ are alkyl groups;
- $R^4$ represents a group selected from a formyl group, a hydroxymethyl group, a 1-hydroxy-1-ethyl group, a 1-hydroxy-1-propyl group, a 1-hydroxy-1-butyl group, and a 2-hydroxy-1-propyl group;
- m is 0 to 2;
- n is 0 or 1; and
- the wavy lines indicate a cis-configuration, a trans-configuration, or a mixture of a cis-configuration and a trans-configuration with respect to position-2 on the cyclopropane ring.

2. The compound according to claim 1, wherein $R^4$ is a group selected from a hydroxymethyl group, a 1-hydroxy-1-ethyl group, a 1-hydroxy-1-propyl group, a 1-hydroxy-1-butyl group, and a 2-hydroxy-1-propyl group.

3. The compound according to claim 2, wherein $R^1$ and $R^3$ are both methyl groups.

4. The compound according to claim 2, wherein $R^1$, $R^2$, and $R^3$ are all methyl groups.

5. The compound according to claim 2, wherein $R^5$ is a methyl group.

6. A flavor and/or fragrance composition, comprising the compound according to claim 1.

7. A food or beverage, a cosmetic, an air-freshener, a daily necessity or grocery, an oral cavity composition, a hair-care product, a skin-care product, a body-cleaning agent, a laundry detergent, a laundry softener, a toiletry product, a fiber or fiber product, a garment, or a pharmaceutical, comprising the flavor and/or fragrance composition according to claim 6.

* * * * *